United States Patent [19]

Seib et al.

[11] Patent Number: 5,110,950
[45] Date of Patent: May 5, 1992

[54] METHOD OF PREPARING 2-PHOSPHORYLATED COMPOUNDS OF ASCORBIC ACID

[75] Inventors: Paul A. Seib; Xiao Y. Wang, both of Manhattan, Kans.

[73] Assignee: Kansas State University Research Foundation, Manhattan, Kans.

[21] Appl. No.: 713,791

[22] Filed: Jun. 12, 1991

[51] Int. Cl.$^5$ ................................. C07F 9/08
[52] U.S. Cl. ..................................... 549/222
[58] Field of Search .......................... 549/222

[56] References Cited

U.S. PATENT DOCUMENTS 4,179,445 12/1979 Sieb et al. ............................. 549/222

FOREIGN PATENT DOCUMENTS 0339486 11/1989 European Pat. Off. ............ 549/222
8700172 1/1987 PCT Int'l Appl. ................. 549/222

Primary Examiner—Marianne Cintins
Assistant Examiner—John Peabody
Attorney, Agent, or Firm—Hovey, Williams, Timmons & Collins

[57] ABSTRACT

A catalyzed synthesis of ascorbate 2-phosphorylated compounds is provided which gives both mono-and polyphosphorylated species in excellent yield using inexpensive, readily available reactants. The method involves forming a reaction mixture of an ascorbic acid reactant such as L-ascorbic acid and a metaphosphate phosphorylating agent (e.g., sodium trimetaphosphate), and carrying out the phosphorylation reaction in the presence of a catalyzing ion selected from the group consisiting of calcium, strontium and barium ion and mixtures thereof, while maintaining the pH of the reaction mixture at a level of from about 3-12. The synthesis is characterized by very short reaction times, preferably from about 15 minutes-2 hours, and moderate temperatures on the order of 18° C.–25° C. Preferably, the catalyzing ion is provided by addition of calcium, strontium or barium hydroxide to the reaction mixture, this serving to also elevate the pH of the system to the desired range.

15 Claims, No Drawings

METHOD OF PREPARING 2-PHOSPHORYLATED COMPOUNDS OF ASCORBIC ACID

BACKGROUND OF THE INVENTION

1. Field of the Invention

The present invention is broadly concerned with an improved, catalyzed synthesis of 2-phosphorylated compounds of ascorbic acid, e.g., L-ascorbate 2-monophosphate (AsMP), and L-ascorbate 2-polyphosphates (AsPP) such as L-ascorbate 2-diphosphate (AsDP) and L-ascorbate 2-triphosphate (AsTP). More particularly, it is concerned with such syntheses wherein an ascorbic acid compound such as L-ascorbic acid (AsA) is reacted with a metaphosphate such as sodium trimetaphosphate (STMP) in an aqueous system at a pH of about 3–12 and in the presence of a reaction-accelerating amount of calcium, strontium or barium ion. The improved methods of the invention give phosphorylated species in excellent yields of greater than 98% under moderate reaction temperatures of about 5° C.–30° C. and extremely short reaction times ranging from 10 minutes to 6 hours.

2. Description of the Prior Art

A method of synthesizing L-ascorbate 2-polyphosphate (AsPP) has been described by Liao and Seib, U.S. Pat. No. 4,647,672, and *J. Ag. Fd. Chem.* 38:355, 1990. In that method, an alkaline solution (pH 11.0) of sodium or potassium L-ascorbate (1.6M) is reacted with sodium trimetaphosphate (1.3 eq.) at 35° C. The reaction is stirred at constant pH 11.0, which is maintained by adding 10M alkali, and after 8 hours, the reaction mixture contains 93% AsPP, 5% unreacted L-ascorbate, and 2% of a 4,5-unsaturated by-product (4,5-ene) formed from 2,6-bis phosphorylated L-ascorbate.

The total reaction mixture containing AsPP can be added to feed as a source of stable vitamin C. All reagents are generally-recognized-as-safe (GRAS), according to Title 21 of the Code of Federal Regulations. In feeding trials with guinea pigs, chicks, and fish, the total reaction mixture has been found free of toxic effects when added to feeds at levels of at least 1000 parts per million in L-ascorbic acid equivalents. Thus, the liquid reaction mixture containing 10–16% by weight of active ingredient (L-ascorbic acid) has been widely used in feeds for fin-fish, shellfish, guinea pigs, and primates.

Despite the utility of the liquid AsPP reaction mixture, several problems remain. First, the reaction time to produce AsPP is long. Secondly, the unreacted L-ascorbate in the reaction mixture is thought to undergo decomposition during long-term storage of the mixture, when it contains sedimented phosphate salts. The sedimented salts generate acidity that catalyzes decomposition of L-ascorbate into carbon dioxide and colored by-products. The gas complicates storage of the reaction mixture, while color is undesirable in food and pharmaceutical applications. Thirdly, the concentration of AsPP in the final reaction mixture is less than 16% by weight of the L-ascorbate moiety, which is too dilute for use in most vitamin and mineral concentrates added to feed, food, and pharmaceuticals. Fourth, dehydration or elimination reactions occur, causing yellow color and a caramel odor. A bland and white vitamin C product is preferred in food and pharmaceutical applications.

U.S. Pat. No. 4,179,445 describes a method of preparing 2-phosphorylated esters of ascorbic acid wherein an ascorbic acid compound is reacted with phosphorous oxychloride in the presence of a tertiary amine such as pyridine in an aqueous system at high pH. This synthesis produces essentially only the 2-phosphated monoester product, and is moreover relatively expensive because of the cost of removing pyridine.

Accordingly, there is a need in the art for an improved synthesis of 2-phosphorylated species of ascorbic acid which gives the desired end products in good yield with no color and odor, using inexpensive starting reactants, and short reaction times.

SUMMARY OF THE INVENTION

The present invention overcomes the problems outlined above and provides a greatly improved method of preparing desirable 2-phosphorylated compounds of L-ascorbic acid and D-erythorbic acid. Broadly speaking, the method of the invention includes the steps of forming a reaction mixture having respective quantities of an ascorbic or erythorbic reactant and a metaphosphate phosphorylating agent in a non-interfering aqueous solvent, and allowing the mixture to react to phosphorylate the ascorbic acid reactant. Very importantly, the synthesis is catalyzed by carrying out the phosphorylating reaction in the presence of a reaction-accelerating amount of an ion selected from the group consisting of calcium, strontium and barium ion and mixtures thereof, while maintaining the reaction mixture pH at a level from about 3–12.

pH maintenance and provision of the catalyzing calcium, strontium or barium ion is effected by adding to the ascorbic acid reactant/metaphosphate reaction mixture an appropriate quantity of calcium, strontium and/or barium hydroxide. In alternative procedures, the catalyzing ion is provided by adding an ion source such as calcium, strontium or barium chloride to the reaction mixture, together with a base for pH maintenance (e.g., sodium or potassium hydroxide).

DESCRIPTION OF THE PREFERRED EMBODIMENTS

A number of ascorbic acid reactants may be used in the context of the present invention. Broadly, the reactant must contain an ascorbic acid moiety; most preferably, the reactant is selected from the group consisting of the stereoisomeric, 6-carbon ascorbic acids and especially L-ascorbic acid (AsA) and D-erythorbic acid, the alkali, alkaline earth metal and tertiary amine salts of the foregoing, as well as derivatives of ascorbic acid having a $C_6$ base-stable blocking group thereon (e.g., 5,6-acetal and 5,6-ketal derivatives of ascorbic acid), and mixtures thereof.

The most preferred phosphorylating agents are the trimetaphosphates, for example, sodium trimetaphosphate. Higher order metaphosphates such as the hexametaphosphates may also be used.

The solvent for the reaction mixture must be aqueous (either pure water or mixed with other species) and essentially non-interfering with the desired phosphorylating reaction. Typically, straight water is used as the solvent.

As indicated previously, the presence of calcium, strontium or barium ion in the reaction mixture has been found to catalyze and materially accelerate the phosphorylation reaction. These ions appear to be unique in their catalyzing effect, inasmuch as magnesium, zinc and aluminum ion have no such effect. Preferably, the calcium, strontium or barium ion is added to the reaction mixture by the simple expedient of adding either calcium, strontium or barium hydroxide thereto. This not only provides the necessary ion, but also elevates the pH of the reaction mixture into the desired range for the reaction. More generally, however, it is only required that calcium, strontium or barium ion be present, typically through addition of a water soluble ion source such as a calcium, strontium or barium salt. Exemplary salts include the chlorides, nitrates and acetates. In such cases, a base should be added to the reaction mixture to elevate the pH of the system, preferred bases in this respect being sodium or potassium hydroxide. It has been found that when reaction pH is below about 9, it is advisable to add salt forms of the catalyzing ion, in order to achieve a desired reaction-accelerating concentration of the ion.

Order of addition of the reactants is not critical. For example, where calcium, strontium or barium hydroxide are employed, it is preferred to first dissolve the ascorbic acid reactant in the aqueous solvent, followed by the hydroxide. After mixing, the metaphosphate is added, and, as the phosphorylation reaction proceeds, the pH is maintained by appropriate addition of calcium, strontium or barium hydroxide (it is normally desirable to select the calcium, strontium or barium hydroxide alone throughout the reaction and avoid mixing these bases). However, the reaction can also be accomplished by initially slurrying the calcium, strontium or barium hydroxide in water, followed by addition of the ascorbic acid compound and the remaining reactants. The concentration of the ascorbate species in the initial reaction mixture is preferred between 1-2M. Under the best conditions, 1.4-1.5M is used.

It is also desirable that in the reaction mixture the molar ratios of the reactants be kept within certain limits. For example, the molar ratio of the phosphorylating agent to the ascorbic acid reactant should be from about 1.1 to 1.5, and most preferably about 1.3. In like manner, the molar ratio of the catalyzing calcium, strontium or barium ion to phosphorus in the reaction mixture should be from about 0.3 to 2.7, depending on pH. The high ratio of 2.7 is most preferred when the reaction pH is approximately 3, whereas the low ratio of 0.3 is most preferred when the reaction pH is about 11.5. The upper limit of the ratio is controlled by gelation of the reaction mixture. In general, a higher ratio of the catalyzing metal ion to phosphorus is used at acidic vs alkaline pH. When reaction pH is at 9.5-10.0, the preferable range of the metal/phosphorus ratio is 0.4 to 0.6, while the most preferred ratio is 0.4, since the final reaction product contains a higher proportion of the 2-triphosphate ester as opposed to the 2-di-or 2-monophosphate ester.

The synthesis of the invention can be readily carried out at room temperatures, although a range of 5° C.-30° C. can be employed. For cost and equipment reasons, reaction temperatures on the order of 18° C.-25° C. are normally preferred.

As indicated, an important feature of the invention involves pH maintenance throughout substantially the entirety of the phosphorylation reaction. The pH should be maintained at a level from about 3-12, more preferably from about 9-11. While it may be possible in some instances to initially add sufficient base to maintain pH control, generally speaking, base addition as needed throughout the course of the reaction is required. This is true even for reactions initiated at low pH's of about 3-4.

The proportions of ascorbate 2-tri. 2-di and 2-monophosphate formed by metal-catalyzed reaction of ascorbate with trimetaphosphate depended generally on reaction pH, metallic ion to phosphorus ratio, temperature and time. The 2-triphosphate ester is preserved in reaction mixtures at pH 7.5-10, a low ratio of catalyzing metal ion to phosphorus appropriate to the chosen reaction pH (e.g. 0.4 for pH 9.5-10, 0.6 for pH 7.5-8), a low temperature of 15° C.-20° C., and a short reaction time commensurate with desired yield. In general, prolonged stirring of a reaction mixture maintained at the set pH converts AsPP to mostly ascorbate 2-monophosphate plus some 2-diphosphate. Hydrolysis of the polyphosphate chain is accelerated by warm temperatures, high pH, and more so by calcium than barium ion.

The following Examples set forth methods for the synthesis of L-ascorbate 2-phosphorylated compounds in accordance with the invention. It should be understood that these Examples are presented for purposes of illustration only, and nothing therein should be taken as a limitation upon the overall scope of the invention.

EXAMPLE 1

Preparation of L-Ascorbate 2-Polyphosphate Using Calcium Hydroxide and Calcium Chloride A 100-mL beaker was fitted with a magnetic stirring bar and a pH electrode. To the beaker, which was placed in a water bath at 25° C., was added, water (4 mL), AsA (1 g, 5.68 mmol, initially 1.42M), calcium chloride (0.2 g), and a suspension of calcium hydroxide (0.5 g) in water (1.0 mL). The starting mixture had pH about 9.5 STMP (2.4 g, 95% purity, 7.45 mmol; Sigma Chemical Co.) was added, and the pH was maintained at 9.5-10.0 by addition of a suspension of calcium hydroxide in water (0.1 g/0.5 mL). The reaction was stopped after 20 minutes, at which time the amount of calcium hydroxide consumed was 0.6 g. The reaction mixture (about 15 mL) was transferred quantitatively to a volumetric flask, and made to volume (100 mL) with HCl (0.3M). An aliquot (0.5 mL) of the reaction mixture was removed, diluted with water (100 fold), and the mixture analyzed for 2-phosphorylated L-ascorbate species using HPLC-UV, or the mixture diluted 10-fold in 0.1M carbonate buffer (pH 10) and its absorbance determined at 259 nm. From the chromatogram of the reaction mixture and standard curves it was calculated that the reaction product contained, on a molar basis, 1.8% unreacted AsA, 10.2% AsMP, 10.2% AsDP, 73.8% AsTP, 5.1% of higher phosphate esters of 2-phosphorylated L-ascorbate, and a trace of 4,5-ene. UV absorbance indicated 104% 2-phosphorylation using molar extinction 16,000 at 259 nm (see Run 7, Table).

A second reaction was run using the same conditions except that the pH of the reaction was maintained at 10.5-11.0. The reaction mixture (about 100 mL) was adjusted to pH 4.5 with 8M HCl followed by addition of calcium chloride (2.2 g). After stirring 5 minutes at 25° C., the mixture was centrifuged at 1700×g to remove insoluble calcium phosphate, and the supernatant was decanted. Water (4×150 mL) was added to the sedimented calcium phosphate, and the mixture was adjusted to pH 4.5 using 8M HCl. After stirring 5 minutes at 25° C. and centrifugation, the supernatants and washings were combined and concentrated to a volume of 30 mL. The concentrate was filtered through Whatman filter paper No. 5, and the filtrate adjusted to pH 7 with 1M sodium hydroxide. Ethanol (50 mL) was added with vigorous stirring, and the precipitate collected by centrifugation. The sediment was washed with 50% ethanol (usually 4×50 mL) until the washings were free of chloride ion. Finally, the sediment was washed with absolute ethanol (50 mL), collected by filtration, and dried in a vacuum dessicator over phosphorus pentoxide. The powdery, white product (about 2.7 g) free of caramel odor contained the following components as determined by HPLC-UV using standard curves derived from reference standards; AsA (none), AsMP (17.8 mole %, based on starting AsA), AsDP (18.5%), AsTP (41.9%), and higher phosphate esters of 2-phosphorylated L-ascorbate (8.3%) determined by difference between total 2-phosphorylation from UV spectroscopy and AsMP plus AsDP plus AsTP. Digestion of the product using phosphatase followed by HPLC-EC (Wang et al. *J. Assoc. Offical. Anal. Chem.*, 76, 1988) showed 88% of starting AsA was present in the calcium AsPP solids.

EXAMPLE 2

Preparation of 5,6-O-Isopropylidene-L-Ascorbate 2-Polyphosphate Using Calcium Hydroxide 5,6-O-Isopropylidene-L-ascorbic acid (IAA) was obtained from Aldrich Chemical Company, Inc. in 98% purity. An equimolar amount of this compound (1.23 g, 5.68 mmol) was used in place of AsA (1 g) and reacted with STMP under conditions described in Example 1. The results are given in Run 17 of the Table.

EXAMPLE 3

Preparation of L-Ascorbate 2-Polyphosphate Using Sodium Hexametaphosphate and Calcium Hydroxide Sodium hexametaphosphate (SHMP) was obtained from Alfa Chemical Company, Inc. in technical grade. One half the equivalent amount of this compound (2.4 g) was used in place of STMP to react with AsA under conditions described in Example 1 for 2-phosphorylation of AsA using calcium hydroxide. The results are given in Run 22 of the Table.

EXAMPLE 4

Preparation of L-Ascorbate 2-Polyphosphate Using Barium Hydroxide

An equal molar amount of barium hydroxide (2.9 g, molar ratio of Ba/P equal to 0.4) was used in place of calcium hydroxide in reaction of AsA with STMP under conditions described in Example 1 for 2-phosphorylation of AsA using calcium hydroxide, except that the pH of the reaction mixture was maintained at 10.5–11.0. The results are given in Run 19 of the Table.

EXAMPLE 5

Calcium L-Ascorbate 2-Monophosphate; Its Preparation and Isolation Starting from AsPP Prepared Using Calcium Hydroxide and Sodium Trimetaphosphate AsA (1 g) was phosphorylated using STMP, Ca(OH)$_2$ and CaCl$_2$ as described in Run 9. The reaction mixture at pH 9.5–10.0 (about 15 mL) was diluted with water to 80 mL, and 33% aqueous calcium chloride (2 mL total, 1 g solids) was added dropwise over 30 minutes. The mixture was stirred at 25° C. for 2 hours, all the while maintaining pH at 10.5–11.0 by addition of a suspension of calcium hydroxide in water (0.3 g/0.6 mL). After 2 hours, the milky appearing reaction mixture (Mixture A) was measured for total volume (about 112 mL) using a graduated cylinder, and an aliquot (1 mL) of Mixture A was dissolved in 0.1M HCl (100 mL). After diluting an additional 10-fold with 0.1M potassium carbonate buffer at pH 10, the mixture had UV absorbance of 0.803 at $\lambda_{max}$262 nm, indicating 99% of phosphorylation of AsA using $\epsilon_{mM}$ 16. The UV absorbance at 313 nm was 0.01, indicating traces of the 4,5-ene compound were present. A second aliquot (0.1 mL) of Mixture A was diluted with water (50 mL), and assayed by HPLC-UV. The chromatogram showed AsMP and AsDP were the principal components in the mixture, along with a trace of AsA; the molar ratio of AsMP/AsDP was 2.3/1.0 using standard curves from reference standards.

To isolate the calcium salt of AsMP and AsDP, Mixture A (about 110 mL) was diluted with water to 200 mL and adjusted to pH 4.5 with 8M HCl. The mixture was centrifuged for 15 minutes at 1700×g, and the supernatant was collected. Water (4×100 mL) was added to the sediment, and the mixture was adjusted to pH 4.5 with 8M HCl. After stirring 5 minutes at 25° C. and centrifugation, the supernatants were combined and concentrated to about 30 mL. The concentrate was filtered through Whatman No. 4 filter paper, and calcium chloride (0.75 g) was added to the filtrate, giving a final molar ratio of phosphorous/Ca of 1:1. After adjusting the mixture to pH 7 using 1M NaOH, absolute ethanol (1.5 volume) was added. The precipitated calcium AsMP and AsDP were collected by centrifugation (15 minutes at 1700×g), and washed free of NaCl using ethanol: water (1.5:1, v/v, 4×50 mL). The final precipitate was suspended in absolute ethanol (5 mL), collected by filtration, and dried under vacuum over phosphorus pentoxide overnight.

The observed yield was 2.2 g of dry solid. A small portion (43 mg) of the dry powder was dissolved in 0.1M HCl, and an aliquot (0.5 mL) of the solution diluted 20-fold with 0.1M potassium carbonate buffer at pH 10. UV absorbance of the solution at 262 nm was 0.69, indicating the combined yield of calcium L-ascorbate 2-monophosphate plus 2-diphosphate (HPLC-UV showed a 2.74:1 molar ratio of AsMP to AsDP) plus other higher phosphate esters of 2-phosphorylated AsA was 78% based on starting AsA. Phosphatase digestion of the product followed by HPLC-EC assay for AsA showed 80% yield based on starting AsA. The purity of the dry solid was 67% based on calcium AsMP plus AsDP.

The calcium phosphate removed from the reaction mixture was dissolved in 0.1M HCl, and the solution combined with the aqueous alcoholic washings of the calcium salts of AsMP/AsDP. Assay by UV spectroscopy showed losses during the isolation step totaled 12–15% of starting AsA.

EXAMPLE 6

Preparation of L-Ascorbate 2-Polyphosphate Using Calcium, Strontium or Barium Salts and Added Base A 1.4M solution of sodium and potassium L-ascorbate was prepared at pH 9.5–10.0 using, respectively, sodium and potassium hydroxide, and calcium, strontium or barium chloride was added at a level equivalent to a molar ratio of Ca, Sr or Ba/P of 0.4. STMP (1.3 eq., based on AsA) was added, and the reaction was allowed to proceed with stirring at 25° C. for 25 minutes, all the while maintaining the pH at 9.5-10.0 by the addition of 10M sodium or potassium hydroxide. (For SrCl$_2$, see Run 23 in Table).

The following Table sets forth the results of a series of phosphorylation reactions, and demonstrates the fact that reaction conditions can be varied widely while still achieving rapid phosphorylation in good yield.

TABLE

Reaction of L-Ascorbic Acid (AsA) or 5,6-O-Isopropylidene-L-Ascorbic Acid (IAA) with Sodium Trimetaphosphate (STMP) Under Different Conditions

| Run No. | AsA,M | Molar Ratio STMP/AsA | Ionic Catalyst | Molar Ratio Cat/P | Cat. Molar Ratio Salt/Base | Temp. °C. | pH | Time (Min.) | Unreacted$^a$ AsA, % | 2-Phosphorylation, % UV Spec$^b$ | HPCL-UV$^c$ |
|---|---|---|---|---|---|---|---|---|---|---|---|
| 1 | 1.42 | 1.3 | Ca | 0.423 | 0.000/0.423 | 20 | 10.5-11.2 | 20 | 4.1 | 97.9 | 92.9 |
| 2 | 1.42 | 1.3 | Ca | 0.423 | 0.060/0.363 | 20 | 9.5-10.0 | 25 | 1.8 | 101.7 | 99.3 |
| 3 | 1.42 | 1.3 | Ca | 0.423 | 0.242/0.181 | 20 | 7.5-8.0 | 45 | 11.2 | 92.3 | 90.1 |
| 4 | 1.42 | 1.3 | Ca | 0.423 | 0.000/0.423 | 20 | 10.5-11.2 | 27 | 3.0 | 100.5 | 94.3 |
| 5 | 1.14 | 1.3 | Ca | 0.423 | 0.000/0.423 | 20 | 10.5-11.2 | 20 | 6.9 | 95.1 | 91.8 |
| 6 | 1.42 | 1.3 | Ca | 0.423 | 0.000/0.423 | 25 | 10.5-11.2 | 15 | 6.7 | 94.7 | 90.5 |
| 7 | 1.42 | 1.3 | Ca | 0.423 | 0.060/0.363 | 25 | 9.5-10.0 | 20 | 1.9 | 103.9 | 99.6 |
| 8 | 1.42$^d$ | 1.3 | Ca | 0.423 | 0.060/0.363 | 25 | 9.5-10.0 | 20 | 1.3 | 101.9 | 99.0 |
| 9 | 1.42 | 1.3 | Ca | 0.423 | 0.060/0.363 | 25 | 9.5-10.0 | 25 | 1.3 | 101.7 | 97.3 |
| 10 | 1.42$^d$ | 1.3 | Ca | 0.423 | 0.060/0.363 | 25 | 9.5-10.0 | 25 | 1.1 | 103.1 | 98.5 |
| 11 | 1.42 | 1.3 | Ca | 0.423 | 0.000/0.363 | 25 | 9.5-10.0$^e$ | 25 | 4.3 | 99.6 | 97.1 |
| 12 | 1.42$^e$ | 1.3 | Ca | 0.423 | 0.000/0.363 | 25 | 9.5-10.0$^e$ | 25 | 4.8 | 96.7 | 99.9 |
| 13 | 1.42 | 1.3 | Ca | 0.423 | 0.000/0.423 | 10 | 10.5-11.2 | 45 | 3.4 | 101.6 | 98.2 |
| 14 | 1.42 | 1.1 | Ca | 0.423 | 0.060/0.363 | 25 | 9.5-10.0 | 25 | 6.2 | 98.9 | 97.2 |
| 15 | 1.42 | 1.2 | Ca | 0.423 | 0.060/0.363 | 25 | 9.5-10.0 | 25 | 1.9 | 103.0 | 98.2 |
| 16 | 1.42$^f$ | 1.3 | Ca | 0.423 | 0.060/0.363 | 25 | 9.5-10.0 | 25 | 1.6 | 101.0 | 103.6 |
| 17 | 1.42$^g$ | 1.3 | Ca | 0.423 | 0.060/0.363 | 25 | 9.5-10.0 | 25 | 2.2 | 101.1 | 84.8 |
| 18 | 1.42 | 1.3 | Ba | 0.423 | 0.000/0.423 | 25 | 9.5-10.0 | 25 | 40.0 | 55.0 | 65.7 |
| 19 | 1.42$^h$ | 1.3 | Ba | 0.423 | 0.000/0.423 | 25 | 10.5-11.2 | 25 | 11.1 | 89.3 | 90.0 |
| 20 | 1.62$^i$ | 1.3 | — | — | — | 35 | 10.5-10.7 | 24 hours | 1.6 | 97.1 | — |
| 21 | 1.42$^j$ | 1.3 | Mg | 0.423 | 0.000/0.423 | 25 | 9.5-10.0 | 22 hours | 7.5 | 92.4 | 91.0 |
| 22 | 1.42$^k$ | 0.65 | Ca | 0.423 | 0.060/0.363 | 25 | 9.5-10.0 | 120 | 29.1 | 66.1 | 58.5 |
| 23 | 1.42$^l$ | 1.3 | Sr | 0.423 | 0.423/0.000 | 25 | 9.5-10.0 | 25 | 0.4 | 103.9 | 101.2 |
| 24 | 1.89 | 1.3 | Ca | 0.423 | 0.060/0.363 | 25 | 9.5-10.0 | 20 | 0.5 | 101.3 | 97.7 |
| 25 | 1.42 | 1.3 | Ca | 0.302 | 0.000/0.302 | 25 | 11.2-11.5 | 15 | 8.5 | 90.9 | 83.6 |
| 26 | 1.42 | 1.3 | Ca | 1.832 | 1.512/0.320 | 25 | 4.2-5.0 | 45 | 3.5 | 96.5 | 94.2 |
| 27 | 1.42 | 1.3 | Ca | 2.672 | 2.297/0.375 | 25 | 3.2-3.8 | 90 | 6.2 | 89.5 | 85.3 |

$^a$Determined by iodine titration.
$^b$UV assay using $\epsilon_{mM}$ 16.0 at 259 nm and pH 10.0.
$^c$HPCL-UV assay using standard curves of reference standards with UV monitor at 250 nm.
$^d$Five grams of starting material (AsA) was used in the reactions.
$^e$Three grams of starting material (AsA) was used in the reactions.
$^f$D-ISOAsA (D-erythorbic) was starting material.
$^g$5,6-0-Isopropylidene L-ascorbic acid was starting material.
$^h$Sodium hydroxide was used to maintain pH.
$^i$Sodium hydroxide was used to maintain pH. No catalyst was added. Data was taken from Liao & Seib. J. Ag. Fd. Chem. 38:355, 1990. The 2-phosphorylated reaction mixture contained 5% of 4,5-ene by-product.
$^j$Sodium hydroxide was used to maintain pH.
$^k$Sodium hexametaphosphate was used as phosphorylation reagent.
$^l$Strotium chloride added to AsA. and mixture adjusted to pH 9.5-10.0. STMP added. and pH maintained by adding 10M sodium hydroxide.

We claim:

1. In a method of synthesizing L-ascorbate 2-phosphorylated compounds including the steps of forming a reaction mixture having respective quantities of an ascorbic acid reactant and a metaphosphate phosphorylating agent in a noninterfering aqueous solvent, and allowing the mixture to react to phosphorylate said reactant, the improvement which comprises the steps of carrying out said phosphorylation reaction in the presence of a phosphorylation reaction-accelerating amount of an ion selected from the group consisting of calcium, strontium and barium ion and mixtures thereof, while maintaining the pH of said reaction mixture at a level of from about 3-12.

2. The method of claim 1, said ascorbic acid reactant being selected from the group consisting of ascorbic acid, the alkali and alkaline earth metal salts of ascorbic acid, the tertiary amine salts of ascorbic acid, derivatives of ascorbic acid having a C$_6$ base-stable blocking group thereon, and mixtures thereof.

3. The method of claim 1, said phosphorylating agent being selected from the group consisting of trimetaphosphate and hexametaphosphate phosphorylating agents and mixtures thereof.

4. The method of claim 3, said agent being sodium trimetaphosphate.

5. The method of claim 1, said solvent is water.

6. The method of claim 1, including the step of allowing said mixture to react for a period of from about 15 minutes to 6 hours.

7. The method of claim 6, said period being from about 15 minutes to 2 hours.

8. The method of claim 1, including the step of maintaining said reaction mixture at a temperature of from about 5° to 30° C. during said reaction.

9. The method of claim 1, including the step of adding a base selected from the group consisting of calcium, strontium and barium hydroxide to said reaction mixture to provide said ion therein.

10. The method of claim 1, including the step of adding a water soluble salt of calcium, strontium or barium to said reaction mixture, along with an amount of extra base for maintaining said pH.

11. The method of claim 10, said salt being selected from the group consisting of the calcium, strontium and barium chlorides, nitrates and acetates, and said extra base being selected from the group consisting of sodium and potassium hydroxide.

12. The method of claim 1, said pH level being from about 9 to 11.

13. The method of claim 1, the molar ratio of said phosphorylating agent to said ascorbic acid reactant being from about 1.1 to 1.5.

14. The method of claim 13, said molar ratio being about 1.3.

15. The method of claim 1, the molar ratio of said ion to phosphorous in said reaction mixture being from about 0.3 to 2.7.

* * * * *